(12) United States Patent
Huelskamp et al.

(10) Patent No.: US 10,220,213 B2
(45) Date of Patent: *Mar. 5, 2019

(54) SYSTEMS AND METHODS FOR SAFE DELIVERY OF ELECTRICAL STIMULATION THERAPY

(71) Applicant: CARDIAC PACEMAKERS, INC., St. Paul, MN (US)

(72) Inventors: Paul Huelskamp, St. Paul, MN (US); Jacob M. Ludwig, Isanti, MN (US); Lance E. Juffer, Lino Lakes, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/015,792

(22) Filed: Feb. 4, 2016

(65) Prior Publication Data

US 2016/0228701 A1 Aug. 11, 2016

Related U.S. Application Data

(60) Provisional application No. 62/113,150, filed on Feb. 6, 2015.

(51) Int. Cl.
*A61N 1/362* (2006.01)
*A61N 1/375* (2006.01)
(Continued)

(52) U.S. Cl.
CPC .......... *A61N 1/3622* (2013.01); *A61N 1/365* (2013.01); *A61N 1/36514* (2013.01); *A61N 1/3756* (2013.01); *A61N 1/37217* (2013.01)

(58) Field of Classification Search
CPC .. A61N 1/3622; A61N 1/365; A61N 1/36514; A61N 1/37217; A61N 1/3756
See application file for complete search history.

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318, 11/2014, Jacobson et al. (withdrawn)
(Continued)

*Primary Examiner* — Alyssa M Alter
(74) *Attorney, Agent, or Firm* — Seager, Tufte & Wickhem LLP

(57) ABSTRACT

Systems and methods for treating arrhythmias are disclosed. In one embodiment an LCP comprises a housing, a plurality of electrodes for sensing electrical signals emanating from outside of the housing, an energy storage module disposed within the housing, and a control module disposed within the housing and operatively coupled to the plurality of electrodes. The control module may be configured to receive electrical signals via two or more of the plurality of electrodes and determine if the received electrical signals are indicative of a command for the LCP to deliver ATP therapy. If the received electrical signals are indicative of a command for the LCP to deliver ATP therapy, the control module may additionally determine whether a triggered ATP therapy mode of the LCP is enabled. If the triggered ATP therapy
(Continued)

mode is enabled, the control module may cause the LCP to deliver ATP therapy via the plurality of electrodes.

18 Claims, 8 Drawing Sheets

(51) Int. Cl.
  *A61N 1/365* (2006.01)
  *A61N 1/372* (2006.01)

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| 4,170,999 A | 10/1979 | Allen et al. | |
| RE30,366 E | 8/1980 | Rasor et al. | |
| 4,243,045 A | 1/1981 | Maas | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,375,817 A | 3/1983 | Engle et al. | |
| 4,384,505 A | 5/1983 | Cotton et al. | |
| 4,387,717 A | 6/1983 | Brownlee et al. | |
| 4,440,173 A | 4/1984 | Hudziak et al. | |
| 4,476,868 A | 10/1984 | Thompson | |
| 4,494,950 A | 1/1985 | Fischell | |
| 4,511,633 A | 4/1985 | Bruno et al. | |
| 4,522,208 A | 6/1985 | Buffet | |
| 4,537,200 A | 8/1985 | Widrow | |
| 4,556,063 A | 12/1985 | Thompson et al. | |
| 4,562,841 A | 1/1986 | Brockway et al. | |
| 4,577,633 A | 3/1986 | Berkovits et al. | |
| 4,587,970 A | 5/1986 | Holley et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,726,380 A | 2/1988 | Vollmann et al. | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,830,006 A | 5/1989 | Haluska et al. | |
| 4,858,610 A | 8/1989 | Callaghan et al. | |
| 4,880,005 A | 11/1989 | Pless et al. | |
| 4,886,064 A | 12/1989 | Strandberg | |
| 4,887,609 A | 12/1989 | Cole, Jr. | |
| 4,895,151 A | 1/1990 | Grevis et al. | |
| 4,928,688 A | 5/1990 | Mower | |
| 4,949,719 A | 8/1990 | Pless et al. | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,107,850 A | 4/1992 | Olive | |
| 5,109,845 A | 5/1992 | Yuuchi et al. | |
| 5,113,859 A | 5/1992 | Funke | |
| 5,113,869 A | 5/1992 | Nappholz et al. | |
| 5,117,824 A | 6/1992 | Keimel et al. | |
| 5,127,401 A | 7/1992 | Grevious et al. | |
| 5,133,353 A | 7/1992 | Hauser | |
| 5,144,950 A | 9/1992 | Stoop et al. | |
| 5,161,527 A | 11/1992 | Nappholz et al. | |
| 5,170,784 A | 12/1992 | Ramon et al. | |
| 5,179,945 A | 1/1993 | Van Hofwegen et al. | |
| 5,188,105 A | 2/1993 | Keimel | |
| 5,193,539 A | 3/1993 | Schulman et al. | |
| 5,193,540 A | 3/1993 | Schulman et al. | |
| 5,228,437 A | 7/1993 | Schroeppel | |
| 5,241,961 A | 9/1993 | Henry | |
| 5,243,977 A | 9/1993 | Trabucco et al. | |
| 5,259,387 A | 11/1993 | dePinto | |
| 5,265,601 A | 11/1993 | Mehra | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,312,441 A | 5/1994 | Mader et al. | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | Decoriolis et al. | |
| 5,354,316 A | 10/1994 | Keimel | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,456,692 A | 10/1995 | Smith, Jr. et al. | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,480,413 A | 1/1996 | Greenhut et al. | |
| 5,507,782 A | 4/1996 | Kieval et al. | |
| 5,522,866 A | 6/1996 | Fernald | |
| 5,540,727 A | 7/1996 | Tockman et al. | |
| 5,545,186 A | 8/1996 | Olson et al. | |
| 5,545,202 A | 8/1996 | Dahl et al. | |
| 5,560,369 A | 10/1996 | Mcclure et al. | |
| 5,571,146 A | 11/1996 | Jones et al. | |
| 5,591,214 A | 1/1997 | Lu | |
| 5,620,466 A | 4/1997 | Haefner et al. | |
| 5,620,471 A | 4/1997 | Duncan | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,706,823 A | 1/1998 | Wodlinger | |
| 5,709,215 A | 1/1998 | Perttu et al. | |
| 5,720,295 A | 2/1998 | Greenhut et al. | |
| 5,720,770 A | 2/1998 | Nappholz et al. | |
| 5,725,559 A | 3/1998 | Alt et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,755,737 A | 5/1998 | Prieve et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |

(56) References Cited

U.S. PATENT DOCUMENTS

| | | |
|---|---|---|
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,893,882 A | 4/1999 | Peterson et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,931,857 A | 8/1999 | Prieve et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,987,352 A | 11/1999 | Klein et al. |
| 5,987,356 A | 11/1999 | DeGroot |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,091,991 A | 7/2000 | Warren |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,330,477 B1 | 12/2001 | Casavant |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,986 B1 | 6/2002 | Sun et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,442,433 B1 | 8/2002 | Linberg |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,106 B2 | 5/2003 | Guck et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,599,250 B2 | 7/2003 | Webb et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,647,434 B1 | 11/2003 | Kamepalli |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,204 B2 | 4/2004 | DeGroot et al. |
| 6,718,212 B2 | 4/2004 | Parry et al. |
| 6,721,597 B1 | 4/2004 | Bardy et al. |
| 6,725,093 B1 | 4/2004 | Ben-Haim et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |

(56) References Cited

U.S. PATENT DOCUMENTS

| | | |
|---|---|---|
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,031,771 B2 | 4/2006 | Brown et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,433 B1 | 8/2007 | Falkenberg et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Heltinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,565,197 B2 | 7/2009 | Haubrich et al. |
| 7,583,995 B2 | 9/2009 | Sanders |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,720,543 B2 | 5/2010 | Dudding et al. |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |

(56) References Cited

U.S. PATENT DOCUMENTS

| | | |
|---|---|---|
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,036,746 B2 | 10/2011 | Sanders |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,684 B2 | 4/2012 | Ghanem et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,437,842 B2 | 5/2013 | Zhang et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,785 B1 | 9/2013 | Crutchfield et al. |
| 8,532,790 B2 | 9/2013 | Griswold |
| 8,538,526 B2 | 9/2013 | Stahmann et al. |
| 8,541,131 B2 | 9/2013 | Lund et al. |
| 8,542,131 B2 | 9/2013 | Jahn |
| 8,543,205 B2 | 9/2013 | Ostroff |
| 8,547,248 B2 | 10/2013 | Zdeblick et al. |
| 8,548,605 B2 | 10/2013 | Ollivier |

(56) References Cited

U.S. PATENT DOCUMENTS

| | | |
|---|---|---|
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,468,772 B2 | 10/2016 | Demmer |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,561,382 B2 | 2/2017 | Persson et al. |
| 9,566,012 B2 | 2/2017 | Greenhut et al. |
| 9,669,230 B2* | 6/2017 | Koop .................. A61N 1/3624 |
| 9,844,675 B2 | 12/2017 | Hareland et al. |
| 2001/0034487 A1 | 10/2001 | Cao et al. |
| 2002/0013613 A1 | 1/2002 | Haller et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |

(56) References Cited

U.S. PATENT DOCUMENTS

| | | |
|---|---|---|
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0171959 A1 | 9/2004 | Stadler et al. |
| 2004/0172067 A1 | 9/2004 | Saba |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0159781 A1 | 7/2005 | Hsu |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0025822 A1* | 2/2006 | Zhang ................ A61N 1/3622 607/4 |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299480 A1 | 12/2007 | Hill |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0138058 A1 | 5/2009 | Cooke et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299438 A1 | 12/2009 | Nolan et al. |
| 2009/0299447 A1 | 12/2009 | Jensen et al. |

(56) References Cited

U.S. PATENT DOCUMENTS

| | | |
|---|---|---|
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0016305 A1 | 1/2012 | Jollota et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303078 A1 | 11/2012 | Li et al. |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |

(56) References Cited

U.S. PATENT DOCUMENTS

| | | |
|---|---|---|
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0330326 A1* | 11/2014 | Thompson-Nauman .................. A61N 1/3918 607/4 |
| 2014/0337922 A1 | 11/2014 | Sievert et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290467 A1 | 10/2015 | Ludwig |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0360041 A1 | 12/2015 | Stahmann et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0228701 A1 | 8/2016 | Huelskamp et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904170 A2 | 4/2008 |
| EP | 1978866 A1 | 10/2008 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9528987 A1 | 11/1995 |
| WO | 9528988 A1 | 11/1995 |
| WO | 0636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006069215 A2 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |

(56) References Cited

FOREIGN PATENT DOCUMENTS

| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self-Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

Notification of Transmittal of the International Search Report and the Written Opinion of the International Searching Authority, or the Declaration for Application No. PCT/US2016/016608, 2016, 11 pages, dated Apr. 21, 2016.

(PCT/US2017/029540) PCT Notification of Transmittal of the International Search Report and the Written Opinion of the International Searching Authority, dated Jun. 28, 2017, 11 pages.

(PCT/US2016/013139) PCT Notification of Transmittal of the International Search Report and the Written Opinion of the International Searching Authority, dated Apr. 14, 2016, 12 pages.

\* cited by examiner

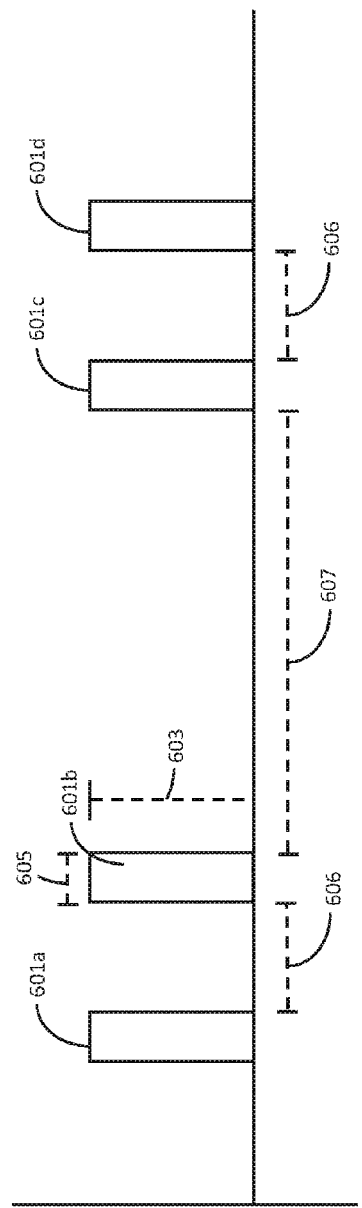
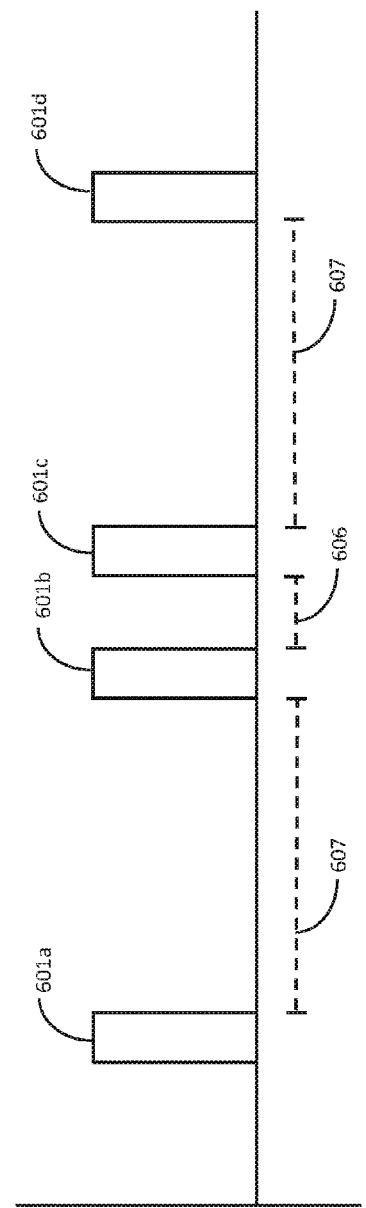
FIG. 6A
FIG. 6B

SYSTEMS AND METHODS FOR SAFE DELIVERY OF ELECTRICAL STIMULATION THERAPY

CROSS REFERENCE TO RELATED APPLICATIONS

This application claims the benefit of U.S. provisional Patent Application Ser. No. 62/113,150 filed on Feb. 6, 2015, the disclosures of each incorporated herein by reference.

TECHNICAL FIELD

The present disclosure generally relates to systems, devices, and methods for treating cardiac arrhythmias, and more particularly, to systems, devices, and methods for detecting cardiac arrhythmias and safely delivering electrical stimulation therapy to treat the detected cardiac arrhythmias.

BACKGROUND

Pacing instruments can be used to treat patients suffering from various heart conditions that may result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, a patient may have multiple implanted devices.

SUMMARY

The present disclosure generally relates to systems, devices, and methods for treating cardiac arrhythmias, and more particularly, to systems, devices, and methods for detecting cardiac arrhythmias and safely delivering electrical stimulation therapy, such as anti-tachycardia pacing (ATP) therapy, to treat the detected cardiac arrhythmias.

In one embodiment, a leadless cardiac pacemaker (LCP) may comprise a housing, a plurality of electrodes for sensing electrical signals emanating from outside of the housing, an energy storage module disposed within the housing, and a control module disposed within the housing and operatively coupled to the plurality of electrodes. The control module may be configured to receive electrical signals via two or more of the plurality of electrodes and determine if the received electrical signals are indicative of a command for the LCP to deliver anti-tachyarrhythmia pacing (ATP) therapy. If the received electrical signals are indicative of a command for the LCP to deliver anti-tachyarrhythmia pacing (ATP) therapy, the control module may additionally determine whether a triggered ATP therapy mode of the LCP is enabled. If the triggered ATP therapy mode is enabled, the control module may cause the LCP to deliver ATP therapy via two or more of the plurality of electrodes.

Alternatively, or additionally, in the above embodiment, if the triggered ATP therapy mode is enabled, the control module may be further configured to determine whether to deliver ATP therapy in response to the command, and if it is determined to deliver ATP therapy, deliver ATP therapy via two or more of the plurality of electrodes.

Alternatively, or additionally, in any of the above embodiments, the control module may be further configured to determine to deliver ATP therapy if the triggered ATP therapy mode is enabled.

Alternatively, or additionally, in any of the above embodiments, the control module may be further configured to determine to deliver ATP therapy if a heart rate, determined from the received electrical signals, is above an arrhythmia threshold.

Alternatively, or additionally, in any of the above embodiments, the control module may be further configured to maintain a count of a number of ATP therapy bursts that have been delivered as part of a delivered ATP therapy, and wherein the controller module is further configured to determine to deliver ATP therapy if the number of ATP therapy bursts has not exceeded a ATP therapy burst count threshold.

Alternatively, or additionally, in any of the above embodiments, if the number of ATP therapy bursts has exceeded the ATP therapy burst count threshold, the control module may be further configured to communicate an error signal to another medical device.

Alternatively, or additionally, in any of the above embodiments, the control module may be further configured to determine a signal morphology type of a cardiac signal received via two or more of the plurality of electrodes, and wherein the controller module is further configured to determine to deliver ATP therapy if the determined signal morphology type is of a predetermined signal morphology type.

Alternatively, or additionally, in any of the above embodiments, the predetermined signal morphology type may comprise a Monomorphic Ventricular Tachycardia (MVT).

Alternatively, or additionally, in any of the above embodiments, the predetermined signal morphology type may comprise a Polymorphic Ventricular Tachycardia (PVT).

Alternatively, or additionally, in any of the above embodiments, the predetermined signal morphology type may comprise a Supra Ventricular Tachycardia (SVT).

Alternatively, or additionally, in any of the above embodiments, the signals indicative of a command for the LCP to deliver anti-tachyarrhythmia pacing (ATP) therapy may comprise a plurality of communication pulses produced by a remote medical device.

Alternatively, or additionally, in any of the above embodiments, the signals indicative of a command for the LCP to deliver anti-tachyarrhythmia pacing (ATP) therapy may comprise a plurality of communication pulses as part of a one-way communication path from a remote medical device.

Alternatively, or additionally, in any of the above embodiments, the plurality of communication pulses may be free from error checking information for error checking the one-way communication path.

Alternatively, or additionally, in any of the above embodiments, the control module may be further configured to, after deliver ATP therapy via two or more of the plurality of electrodes, deliver post shock pacing therapy.

Alternatively, or additionally, in any of the above embodiments, the control module may be further configured to deliver post shock packing therapy for between about 30-60 seconds after delivering ATP therapy.

In another embodiment, a leadless cardiac pacemaker (LCP) may comprise a housing, a plurality of electrodes for sensing electrical signals emanating from outside of the housing, an energy storage module disposed within the housing, and a control module disposed within the housing and operatively coupled to the plurality of electrodes. The control module may be configured to receive electrical signals via two or more of the plurality of electrodes and determine if the received electrical signals are indicative of a command for the LCP to deliver anti-tachyarrhythmia pacing (ATP) therapy. If the received electrical signals are indicative of a command for the LCP to deliver anti-tachyarrhythmia pacing (ATP) therapy, the control module may further be configured to determine whether a triggered ATP therapy mode of the LCP is enabled. If the triggered ATP therapy mode is enabled, the control module may cause the LCP to deliver ATP therapy via two or more of the plurality of electrodes.

Alternatively, or additionally, in the above embodiment, if the triggered ATP therapy mode is enabled, the control module may be further configured to determine whether to deliver ATP therapy in response to the command, and if it is determined to deliver ATP therapy, deliver ATP therapy via two or more of the plurality of electrodes.

Alternatively, or additionally, in any of the above embodiments, the control module may be further configured to determine to deliver ATP therapy if the triggered ATP therapy mode is enabled.

Alternatively, or additionally, in any of the above embodiments, the control module may be further configured to determine to deliver ATP therapy if a heart rate, determined from the received electrical signals, is above an arrhythmia threshold.

Alternatively, or additionally, in any of the above embodiments, the control module may be further configured to maintain a count of a number of ATP therapy bursts that have been delivered as part of a delivered ATP therapy, and wherein the controller module is further configured to determine to deliver ATP therapy if the number of ATP therapy bursts has not exceeded a ATP therapy burst count threshold.

Alternatively, or additionally, in any of the above embodiments, the control module may be further configured to determine a signal morphology type of a cardiac signal received via two or more of the plurality of electrodes, and wherein the controller module is further configured to determine to deliver ATP therapy if the determined signal morphology type is of a predetermined signal morphology type.

Alternatively, or additionally, in any of the above embodiments, the predetermined signal morphology type may comprise a Monomorphic Ventricular Tachycardia (MVT).

Alternatively, or additionally, in any of the above embodiments, the predetermined signal morphology type may comprise a Polymorphic Ventricular Tachycardia (PVT).

Alternatively, or additionally, in any of the above embodiments, the predetermined signal morphology type may comprise a Supra Ventricular Tachycardia (SVT).

In yet another embodiment, a leadless cardiac pacemaker (LCP) may comprise a housing, a plurality of electrodes for sensing electrical signals emanating from outside of the housing, an energy storage module disposed within the housing, and a control module disposed within the housing and operatively coupled to the plurality of electrode. The control module may be configured to receive electrical signals via two or more of the plurality of electrodes and determine if the received electrical signals are indicative of a command for the LCP to deliver anti-tachyarrhythmia pacing (ATP) therapy. If the received electrical signals are indicative of a command for the LCP to deliver anti-tachyarrhythmia pacing (ATP) therapy, the control module may be configured to deliver ATP therapy via two or more of the plurality of electrodes. The control module may further be configured to maintain a measure related to an amount of ATP therapy delivered as part of the delivered ATP therapy within a predetermined period of time and to continue to allow delivery of ATP therapy if the measure related to the amount of ATP therapy delivered within the predetermined period of time has not exceeded a predetermined ATP therapy threshold. The control may also stop delivery of ATP therapy if the measure related to the amount of ATP therapy delivered within the predetermined period of time has exceeded the predetermined ATP therapy threshold.

Alternatively, or additionally, in any of the above embodiments, the predetermined period of time may be between one hour and twenty-four hours.

Alternatively, or additionally, in any of the above embodiments, the measure related to the amount of ATP therapy delivered as part of the delivered ATP therapy within the predetermined period of time may correspond to an ATP therapy delivered count that is indicative of a number of times a command is received that results in the LCP delivering ATP therapy within the predetermined period of time.

Alternatively, or additionally, in any of the above embodiments, the measure related to the amount of ATP therapy delivered as part of the delivered ATP therapy within the predetermined period of time may correspond to an ATP burst count that is indicative of a number of ATP bursts that are delivered within the predetermined period of time.

Alternatively, or additionally, in any of the above embodiments, the received electrical signals may comprise a plurality of communication pulses produced by a remote medical device.

Alternatively, or additionally, in any of the above embodiments, the received electrical signals may comprise a plurality of communication pulses as part of a one-way communication path from a remote medical device.

Alternatively, or additionally, in any of the above embodiments, the plurality of communication pulses may be free from error checking information for error checking the one-way communication path.

Alternatively, or additionally, in any of the above embodiments, after delivering ATP therapy, the LCP may be further configured to enter a post shock pacing mode.

In still another embodiment, a leadless cardiac pacemaker (LCP) may comprise a housing, a plurality of electrodes for sensing electrical signals emanating from outside of the housing, an energy storage module disposed within the housing, and a control module disposed within the housing and operatively coupled to the plurality of electrodes. The control module may be configured to receive electrical signals via two or more of the plurality of electrodes and determine if the received electrical signals are indicative of a command for the LCP to deliver anti-tachyarrhythmia pacing (ATP) therapy. If the received electrical signals are indicative of a command for the LCP to deliver anti-tachyarrhythmia pacing (ATP) therapy, the control module may further determine whether a triggered ATP therapy mode of the LCP is enabled and determine whether a heart rate determined from the received electrical signals is above an arrhythmia threshold. If the triggered ATP therapy mode is enabled and the heart rate is above the arrhythmia threshold, the control module may cause the LCP to deliver ATP therapy via two or more of the plurality of electrodes.

Alternatively, or additionally, in any of the above embodiments, the control module may further maintain a measure related to the amount of ATP therapy delivered within a predetermined period of time, and wherein the control module may be further configured to determine if the measure related to the amount of ATP therapy delivered within the predetermined period of time exceeds a predetermined ATP therapy threshold, and only cause the LCP to deliver ATP therapy via two or more of the plurality of electrodes if the triggered ATP therapy mode is enabled, the heart rate is above the arrhythmia threshold, and the measure related to the amount of ATP therapy delivered within the predetermined period of time does not exceed the predetermined ATP therapy threshold.

Alternatively, or additionally, in any of the above embodiments, the predetermined period of time is between one hour and twenty-four hours.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIGS. 6A-6B illustrate example communication pulse sequences, in accordance with yet another embodiment of the present disclosure;

Figure 1:
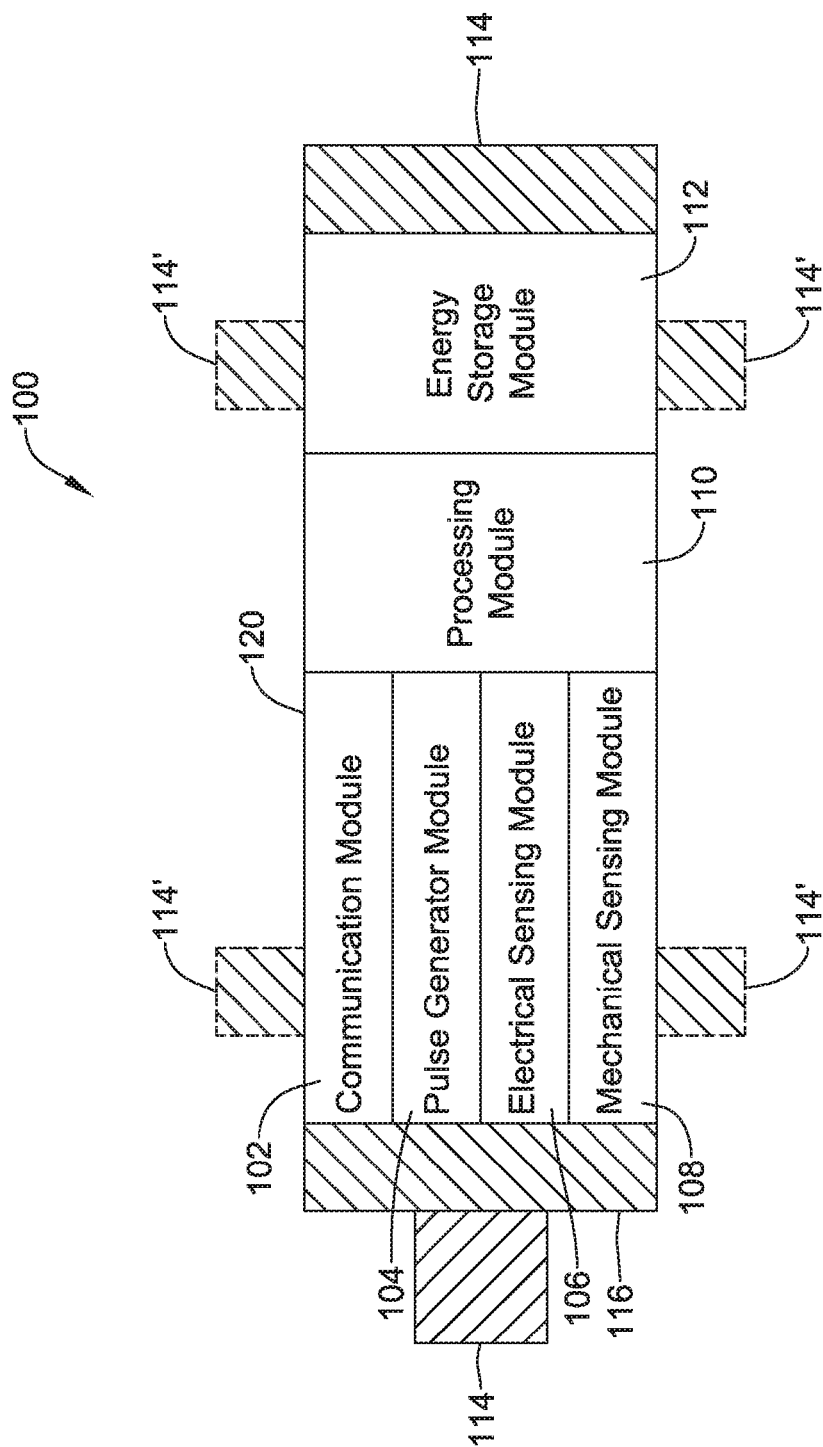
FIG. 1 is a schematic block diagram of an illustrative leadless cardiac pacemaker (LCP) according to one embodiment of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for detecting and safely treating cardiac arrhythmias. In some medical device systems including a plurality of medical devices, a first device of the system may determine occurrences of cardiac arrhythmias and may command another device to deliver electrical stimulation therapy. In such system, the first device may communicate a command to the second device, where upon reception of the command, the second device initiates delivery of the electrical stimulation therapy. In some medical device systems, it may be important to implement one or more safeguards to help ensure that the second medical device is not incorrectly delivering electrical stimulation therapy. This disclosure details various example safeguard techniques.

FIG. 1 is a conceptual drawing of an exemplary leadless cardiac pacemaker (LCP) that may be implanted into a patient and may operate to sense physiological signals and parameters and deliver one or more types of electrical stimulation therapy to tissues of the patient. Example electrical stimulation therapy includes anti-tachycardia pacing (ATP) therapy, cardiac resynchronization therapy (CRT), bradycardia therapy, various types of pacing therapy including rate responsive pacing therapy, and/or the like. As can be seen in FIG. 1, LCP 100 may be a compact device with all components housed within LCP 100 or directly on housing 120. The illustrative LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 but exposed to the tissue and/or blood surrounding LCP 100. Electrodes 114 may generally conduct electrical signals to and from LCP 100 and the surrounding tissue and/or blood. Such electrical signals can include communication pulses, electrical stimulation pulses, and intrinsic cardiac electrical signals. Intrinsic cardiac electrical signals may include electrical signals generated by the heart, and may be represented by an electrocardiogram (ECG). Electrodes 114 can be made up of one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, electrodes 114 may have an insulative portion that electrically isolates electrodes 114 from adjacent electrodes, housing 120, and/or other portions of LCP 100. Some or all of electrodes 114 may be spaced from housing 120 and connected to housing 120 and/or other components of LCP 100 through connecting wires. In such embodiments, the electrodes 114 may be placed on a on a tail that extends from the housing 120. As shown in FIG. 1, in some embodiments, LCP 100 may additionally include electrodes 114'. Electrodes 114' are similar to electrodes 114 except that electrodes 114' are disposed on the sides of LCP 100 and increase the number of electrodes by which LCP 100 may deliver communication pulses and electrical stimulation pulses and/or sense for intrinsic cardiac electrical signals, communication pulses, and/or electrical stimulation pulses.

Electrodes 114 and/or 114' may have any of a variety of sizes and/or shapes, and may be spaced at any of a variety of distances. For example, electrodes 114 may have a diameter of two to twenty millimeters (mm). However, in other embodiments, electrodes 114 and/or 114' may have a diameter of two, three, five, seven millimeters (mm), or any other suitable diameter, dimension and shape. Example lengths for electrodes 114 and/or 114' include a length of zero, one, three, five, ten millimeters (mm), or any other suitable length. As used herein, the length is a dimension of electrodes 114 and/or 114' that extends away from housing 120. Additionally, at least some of electrodes 114 and/or 114' may be spaced from one another by a distance of twenty, thirty, forty, fifty millimeters (mm), or any other suitable distance. The electrodes 114 and/or 114' of a single device may have different sizes with respect to each other, and the spacing of the electrodes on the device may not be uniform.

Communication module 102 may be electrically coupled to electrodes 114 and/or 114' and configured to deliver communication pulses to tissues of the patient for communicating with other devices such as sensors, programmers, other medical devices, and the like. Communication pulses, as used herein, may be any modulated signal that conveys information to another device, either by itself or in conjunction with one or more other modulated signals. In some embodiments, communication pulses are limited to only including sub-threshold signals which convey information. Such other devices may be located either external or internal to the patient's body. Communication module 102 may additionally be configured to sense for communication pulses delivered by the other devices, which are located externally to LCP 100. Irrespective of the location, LCP and the other devices may communicate with each other via communication module 102 to accomplish one or more desired functions. Some example functions include storing communicated data, using communicated data for determining occurrences of arrhythmias, coordinating delivery of electrical stimulation therapy such as triggering an ATP therapy, and/or other functions.

LCP 100 and the other devices may use the delivered communication pulses to communicate raw information, processed information, messages, and/or other data. Raw information may include information such as sensed electrical signals (e.g. a sensed ECG), signals gathered from coupled sensors, and the like. In some embodiments, the raw information may include signals that have been filtered using one or more signal processing techniques. Processed information may include any information that has been determined by LCP 100. For example, processed information may include a determined heart rate, timings of determined heartbeats, timings of other determined events, determinations of threshold crossings, expirations of monitored time periods, and determined parameters such as activity parameters, blood-oxygen parameters, blood pressure parameters, heart sound parameters, and the like. Messages may include instructions or commands directing another device to take action, notifications of imminent actions of the sending device, requests for reading from the receiving device or writing data to the receiving device.

In at least some embodiments, communication module 102 (or LCP 100) may further include switching circuitry to selectively connect one or more of electrodes 114 and/or 114' to communication module 102 in order to select via which electrodes 114 and/or 114' communication module 102 delivers the communication pulses. Additionally, communication module 102 may be configured to use one or more methods for communicating with other devices. For example, communication module 102 may communicate via conducted signals, radiofrequency (RF) signals, optical signals, acoustic signals, inductive coupling, and/or any other signals or methods suitable for communication.

Pulse generator module 104 of LCP 100 may also be electrically connected to one or more of electrodes 114 and/or 114'. Pulse generator module 104 may be configured to generate electrical stimulation pulses and deliver the electrical stimulation pulses to tissues of a patient via electrodes 114 and/or 114' electrodes in order to effectuate one or more electrical stimulation therapies. Electrical stimulation pulses as used herein are meant to encompass any electrical signals that may be delivered to tissue of a patient for purposes of treatment of any type of disease or abnormality. When used to treat heart diseases or abnormalities, the electrical stimulation pulses may generally be configured so as to capture the heart of the patient—cause the heart to contract in response to the delivered electrical stimulation pulse. One example of these electrical stimulation pulses include pacing pulses. In at least embodiments where pulse generator 104 is configured to generate specific types of electrical stimulation pulses termed defibrillation/cardioversion pulses, pulse generator module 104 may include one or more capacitor elements or other charge storage devices.

Pulse generator module 104 may include capability to modify the electrical stimulation pulses, such as by adjusting a pulse width or amplitude of the electrical stimulation pulses, in order to ensure that the delivered electrical stimulation pulses consistently capture the heart. Pulse generator module 104 may use energy stored in energy storage module 112 to generate the electrical stimulation pulses. In at least some embodiments, pulse generator module 104 (or LCP 100) may further include switching circuitry to selectively connect one or more of electrodes 114 and/or 114' to pulse generator module 104 in order to select via which electrodes 114 and/or 114' pulse generator 104 delivers the electrical stimulation pulses.

In some embodiments, LCP 100 may include electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114'. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, blood-oxygen sensors, and/or other sensors which measure one or more physiological parameters of the heart and/or patient. Mechanical sensing module 108 may gather signals from the sensors indicative of the various physiological parameters. Both electrical sensing module 106 and mechanical sensing module 108 may be further connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module.

Processing module 110 may be configured to control the operation of LCP 100. For example, processing module 110 may be configured to receive cardiac electrical signals from electrical sensing module 106 and/or physiological signals from mechanical sensing module 108. Based on the received signals, processing module 110 may determine occurrences and types of arrhythmias. Processing module 110 may further receive information from communication module 102. In some embodiments, processing module 110 may additionally use such received information to determine occurrences and types of arrhythmias. However, in other embodiments, LCP 100 may use the received information instead of the signals received from electrical sensing module 106 and/or mechanical sensing module 108—for instance if the received information is more accurate than the signals received from electrical sensing module 106 and/or mechanical sensing module 108 or if electrical sensing module 106 and/or mechanical sensing module 108 have been disabled or omitted from LCP 100.

Based on any determined arrhythmias, processing module 110 may then control pulse generator module 104 to generate electrical stimulation pulses in accordance with one or more electrical stimulation therapies to treat the determined arrhythmias. For example, processing module 110 may control pulse generator module 104 to generate pacing pulses with varying parameters and in different sequences to effectuate one or more electrical stimulation therapies. In controlling pulse generator module 104 to deliver bradycardia pacing therapy, processing module 110 may control pulse generator module 104 to deliver pacing pulses designed to capture the heart of the patient at a regular interval to prevent the heart of a patient from falling below a predetermined threshold. For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Processing module 110 may then control pulse generator module 104 to reduce the rate of delivered pacing pulses down to a safe level. In CRT, processing module 110 may control pulse generator module 104 to deliver pacing pulses in coordination with another device to cause the heart to contract more efficiently. Additionally, in cases where pulse generator module 104 is capable of generating defibrillation and/or cardioversion pulses for defibrillation/cardioversion therapy, processing module 110 may control pulse generator module 104 to generate such defibrillation and/or cardioversion pulses. In other embodiments, processing module 110 may control pulse generator module 104 to generate electrical stimulation pulses to provide electrical stimulation therapies different than those described herein to treat one or more detected cardiac arrhythmias.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may ensure that LCP 100 is able to provide effective delivery of electrical stimulation therapy.

In some embodiments, processing module 110 may further control communication module 102 to send information to other devices. For example, processing module 110 may control communication module 102 to generate one or more communication pulses for communicating with other devices of a system of devices. For instance, processing module 110 may control communication module 102 to generate communication pulses in particular sequences, where the specific sequences convey different data to other devices. Communication module 102 may also conduct any received communication signals to processing module 110 for potential action by processing module 110.

In further embodiments, processing module 110 may additionally control switching circuitry by which communication module 102 and pulse generator module 104 deliver communication pulses and electrical stimulation pulses to tissue of the patient. As described above, both communication module 102 and pulse generator module 104 may include circuitry for connecting one or more electrodes 114 and/114' to communication module 102 and pulse generator module 104 so those modules may deliver the communication pulses and electrical stimulation pulses to tissue of the patient. The specific combination of one or more electrodes by which communication module 102 and pulse generator module 104 deliver communication pulses and electrical stimulation pulses influence the reception of communication pulses and/or the effectiveness of electrical stimulation pulses. Although it was described that each of communication module 102 and pulse generator module 104 may include switching circuitry, in some embodiments LCP 100 may have a single switching module connected to all of communication module 102, pulse generator module 104, and electrodes 114 and/or 114'. In such embodiments, processing module 110 may control the single switching module to connect modules 102/104 and electrodes 114/114'.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby increasing the battery life of LCP 100. In other embodiments, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional embodiments, may further include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110 may have address lengths of, for example, eight bits. However, in other embodiments, the memory circuit may have address lengths of sixteen, thirty-two, or sixty-four bits, or any other bit length that is suitable. Additionally, the memory circuit may be volatile memory, non-volatile memory, or a combination of both volatile memory and non-volatile memory.

Energy storage module 112 may provide a power source to LCP 100 for its operations. In some embodiments, energy storage module 112 may be a non-rechargeable lithiumbased battery. In other embodiments, the non-rechargeable battery may be made from other suitable materials known in the art. Because LCP 100 is an implantable device, access to LCP 100 may be limited. In such circumstances, it is necessary to have sufficient energy capacity to deliver therapy over an extended period of treatment such as days, weeks, months, or years. In some embodiments, energy storage module 112 may a rechargeable battery in order to facilitate increasing the useable lifespan of LCP 100. In still other embodiments, energy storage module 112 may be other types of energy storage devices such as capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any number of fixation or anchoring mechanisms. For example, anchor 116 may include one or more pins, staples, threads, screws, helix, tines, and/or the like. In some embodiments, although not shown, anchor 116 may include threads on its external surface that may run along at least a partial length of anchor 116. The threads may provide friction between the cardiac tissue and the anchor to help fix anchor 116 within the cardiac tissue. In other embodiments, anchor 116 may include other structures such as barbs, spikes, or the like to facilitate engagement with the surrounding cardiac tissue.

Figure 2:
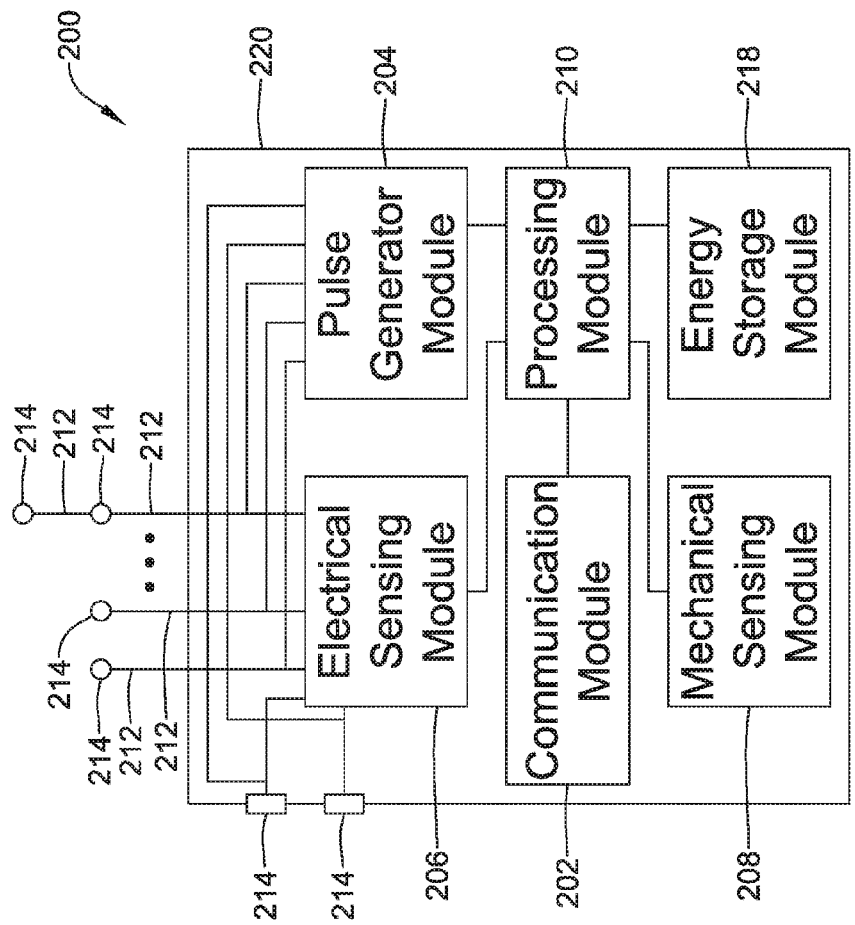
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). In such embodiments, MD 200 may be configured to deliver various types of electrical stimulation therapy, including, for example, defibrillation therapy.

Figure 3:
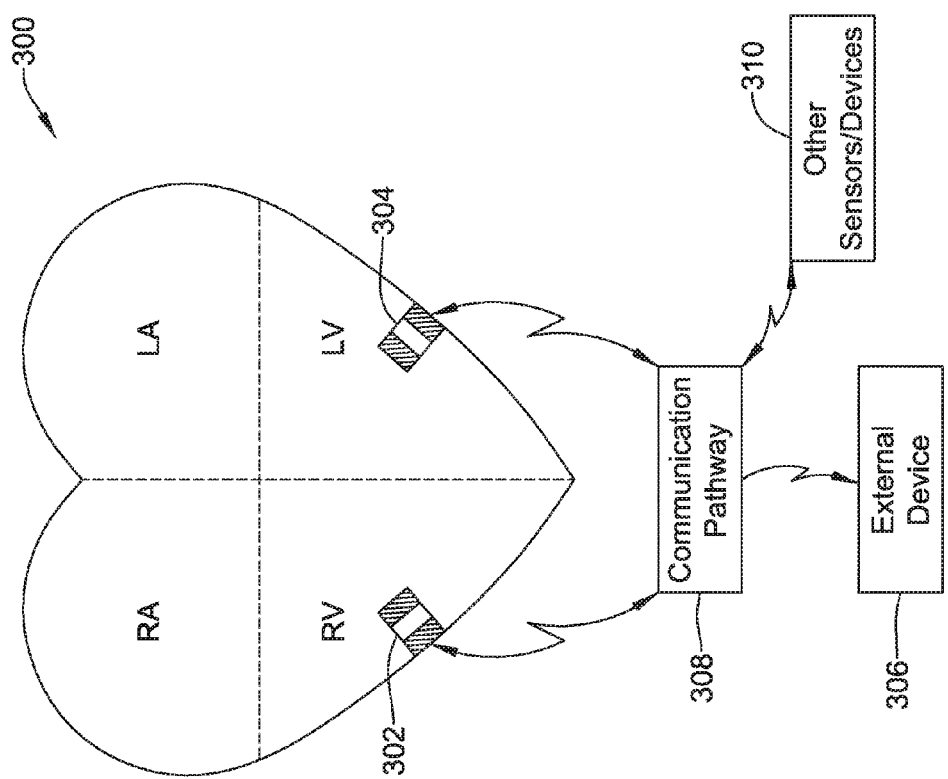
FIG. 3 is a schematic diagram of an exemplary medical system that includes multiple LCPs and/or other devices in communication with one another

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such embodiments, the delivered conducted communication signals (e.g. pulses) may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pules may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
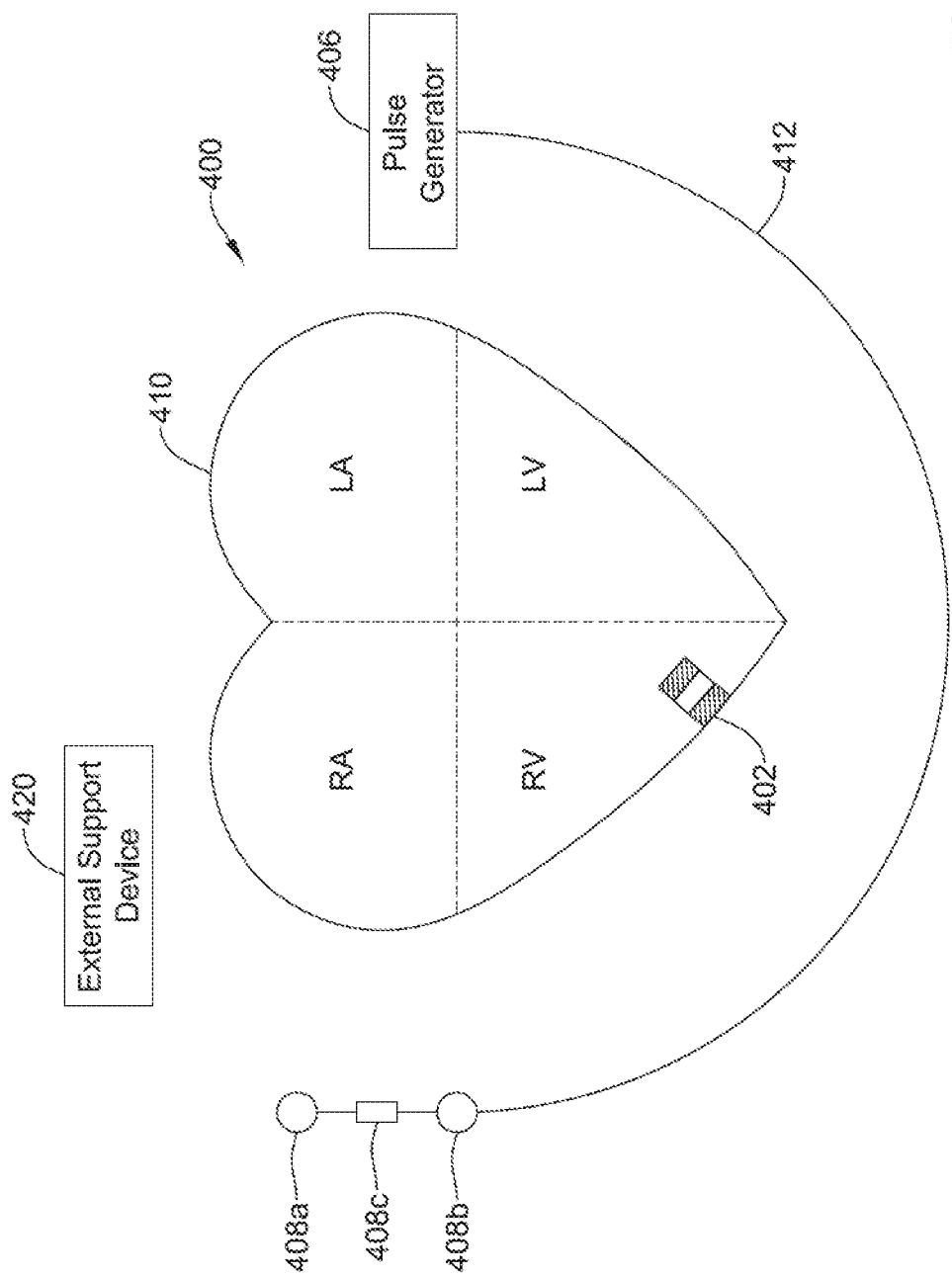
FIG. 4 is a schematic diagram of a system including an LCP and another medical device, in accordance with another embodiment of the present disclosure.
Figure 5:
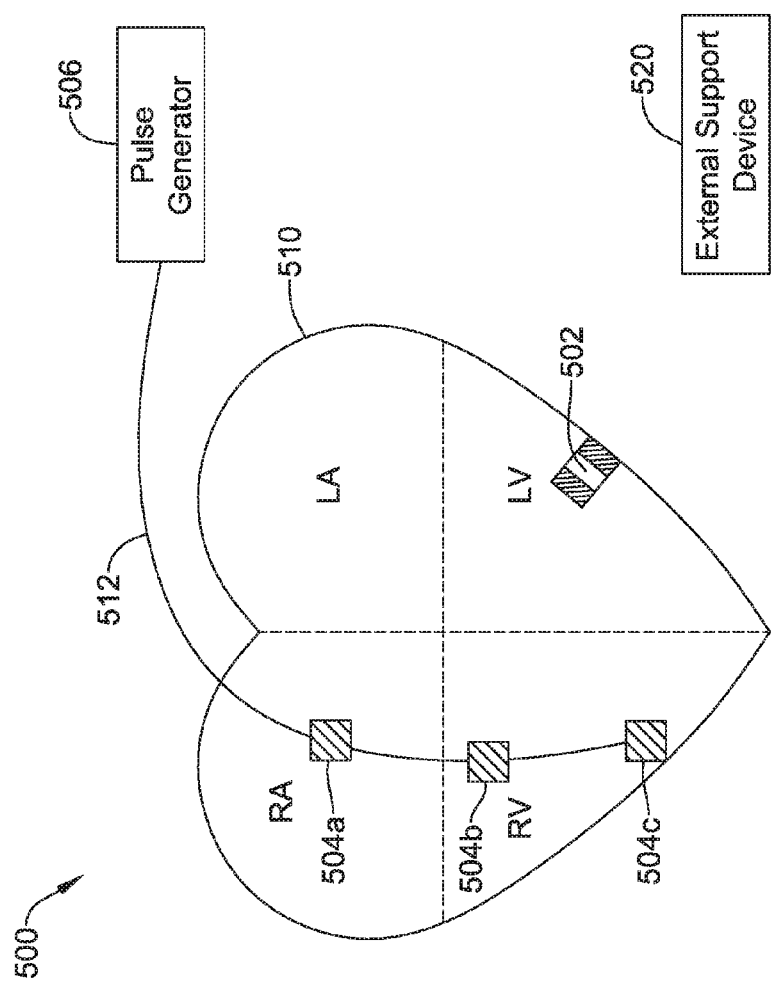
FIG. 5 is a schematic diagram of a system including a leadless cardiac pacemaker (LCP) and another medical device, in accordance with yet another embodiment of the present disclosure.

FIGS. 4 and 5 show illustrative medical device systems that may be configured to operate according to techniques disclosed herein. For example, the systems may include multiple devices that are implanted within a patient and are configured to sense physiological signals, determine occurrences of cardiac arrhythmias, and deliver electrical stimulation to treat detected cardiac arrhythmias. In FIG. 4, an LCP 402 is shown fixed to the interior of the right ventricle of the heart 410, and a pulse generator 406 is shown coupled to a lead 412 having one or more electrodes 408a-408c. In some cases, the pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

In FIG. 5, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, LCP 502 may communicate with the implantable cardiac pacemaker (ICP) and/or an implantable cardioverter-defibrillator (ICD), such as via communication pathway 308. As with FIG. 4, the locations of LCP 502, pulse generator 506, lead 512, and electrodes 504a-c depicted in FIG. 5 are just exemplary. In other embodiments of system 500, LCP 502 may be positioned in the right ventricle, right atrium, or left atrium of the heart, as desired. In still other embodiments, LCP 502 may be implanted externally adjacent to heart 510 or even remote from heart 510. Additionally, in some embodiments lead 512 and/or electrodes 504a-c may be disposed in different chambers of heart 510, or pulse generator may include additional leads and/or electrodes that are disposed within or adjacent to heart 510.

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted communication mode. In some embodiments, communication between the LCP 402 and external support device 420 is accomplished by sending communication information through the pulse generator 406. However, in other embodiments, communication between the LCP 402 and external support device 420 may be via a communication module.

FIGS. 4-5 only illustrate a few embodiments of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406 or 506, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different than those depicted in FIGS. 4 and 5. Accordingly, it should be recognized that numerous other medical device systems, different from those depicted in FIGS. 4 and 5, may be operated in accordance with techniques disclosed herein. As such, the embodiments systems shown in FIGS. 4 and 5 should not be viewed as limiting in any way.

Using the system of FIG. 4 as one exemplary embodiment, LCP 402 and the ICD (which can be a non-subcutaneously implanted device, or a subcutaneously implanted device—an SICD), which can include pulse generator 406, may determine occurrences of cardiac arrhythmias and coordinate to safely deliver electrical stimulation therapy. In one embodiment, after the ICD determines an occurrence of a cardiac arrhythmia, such as a tachyarrhythmia, the ICD may communicate a command to LCP 402 to deliver ATP therapy.

FIGS. 6A-6B depict example electrical signals representing communication pulse sequences that the ICD may communicate to LCP 402 to command LCP 402 to deliver electrical stimulation therapy. In the embodiments of FIGS. 6A-6B, the communication pulses may have a predefined amplitude and pulse width and may be spaced apart in a predetermined pattern. For instance, in the embodiment of FIG. 6A, the communication pulse sequence includes four individual communication pulses 601a-601d all having a common amplitude 603 and pulse width 605. Communication pulses 601a and 601b are spaced apart from one another by a time delay 606. Likewise, communication pulses 601c and 601d are spaced apart from one another by the time delay 606. Pulses 601b and 601c are spaced apart by a longer time delay 607. This may provide a relatively simple communication pulse pattern that should be distinguishable from noise that might be present on the electrodes of the LCP 402.

FIG. 6B depicts another embodiment. In this embodiment, the sequence of communication pulse starts with a single pulse 601a, followed by two communication pulses 601b and 601c after a time delay 607. Communication pulses 601b and 601c are spaced part by a shorter time delay 606. Finally, communication pulse 601d is spaced apart from communication pulse 601c by time delay 607. Again, this may provide another relatively simple communication pulse pattern that should be distinguishable from noise that might be present on the electrodes of the LCP 402.

It should be understood that the example communication pulse sequences depicted in FIGS. 6A-6B are only illustrative. In other embodiments, pulse amplitudes 603 and pulse widths 605 may be varied between the individual communication pulses 601a-601d. In additional or alternative embodiments, the spacing between 601a-601d may be different than depicted in FIGS. 6A-6B. In still further embodiments, the number of communication pulses in the communication pulse sequence indicating a command for LCP 402 to deliver ATP therapy may have more or fewer communication pulses. In at least some embodiments, the communication pulse sequence may not include any error checking information (e.g. parity bits) that may be used to error check the communication pulse sequence as a valid communication pulse sequence—e.g. that it came from the ICD and is a valid command for LCP 402 to deliver ATP therapy.

In some example systems, the ICD and LCP 402 may only communicate via a one-way communication path whereby the ICD sends communications to the LCP 402, but the LCP 402 does not send communications back to the ICD. In such embodiments, LCP 402 may listen for the predetermined communication pulse sequence indicating a command for LCP 402 to deliver ATP therapy, such as the illustrative communication pulse sequences shown in FIGS. 6A-6B. Upon receiving a predetermined pulse sequence, LCP 402 may deliver ATP therapy. In systems that employ one-way communication from the ICD to LCP 402 and/or that do not have any error checking scheme in place to help ensure the validity of the received communication pulse sequence commanding LCP 402 to deliver ATP therapy, it may beneficial to include one or more safeguard features so that LCP 402 does not erroneously deliver ATP therapy when not actually commanded to by the ICD (e.g. due to noise or the like). Delivery of ATP therapy when the therapy is unnecessary may be harmful to the patient under some circumstances.

One example safeguard feature that LCP 402 may provide is a triggered ATP therapy mode. For example, after receiving the electrical signals indicative of a command to deliver ATP therapy, LCP 402 may check to see if its triggered ATP therapy mode is enabled. If the triggered ATP therapy mode is enabled, LCP 402 may then proceed. If the triggered ATP therapy mode is not enabled, LCP 402 may not proceed to delivery ATP therapy. In general, the triggered ATP therapy mode may comprise a mode wherein LCP 402 will deliver ATP therapy in response to receiving the electrical signals indicative of a command to deliver ATP therapy. In some embodiments of a triggered ATP therapy mode, while an ATP therapy mode is active, LCP 402 may still deliver ATP therapy in response to other inputs, for example sensed cardiac electrical signals. However, in other embodiments, when a triggered ATP therapy mode is active, LCP 402 may only deliver ATP therapy in response to receiving the electrical signals indicative of a command to deliver ATP therapy.

The triggered ATP therapy mode may be enabled, for example, only when LCP 402 is part of a medical system where one of the other devices in the system is configured to communicate a command to the LCP 402 to deliver ATP therapy. Due to the relatively simplistic nature of the communication pulse sequence, in some instances it may be possible for LCP 402 to receive/interpret noise signals that replicate or can be interpreted as the communication pulse sequence of the command for the LCP 402 to deliver ATP therapy. In embodiments where LCP 402 is not part of a system where a device can communicate a command to the LCP 402 to deliver ATP therapy, disabling the triggered ATP therapy mode of LCP 402 may help prevent LCP 402 from erroneously delivering ATP therapy due to received noise signals.

This triggered ATP therapy mode safety feature may be particularly useful in situations where LCP 402 does not communicate with other devices, or at least the devices that may communicate a command to LCP 402 to deliver ATP therapy, as LCP 402 may have no capability to double check with the other devices or confirm receipt of the command. The triggered ATP therapy mode may also be useful in systems where there is no error checking scheme to validate that the command came from another valid medical device and is a valid command. However, such a safety feature may be useful in systems that do include two-way communication and/or an error checking scheme as well.

In other embodiments, either in addition to the triggered ATP therapy mode or as an alternative to the triggered ATP therapy mode, LCP 402 may include an arrhythmia threshold safety feature. For example, the ICD of the above described system may monitor a heart rate parameter. When the ICD detects that the heart rate has risen to be equal to or greater than a predetermined threshold, the ICD may determine an occurrence of an arrhythmia, such as a tachycardia. When this happens, the ICD may communicate a command to LCP 402 to deliver ATP therapy. However, in some cases, the ICD may erroneously determine that the heart rate is above the predetermined threshold. For instance, the ICD may count R-waves to determine a heart rate. In some situations, the ICD may also erroneously count T-waves or P-waves as R-waves, thereby erroneously detecting a heart rate greater than the true heart rate.

In these embodiments where LCP 402 includes an arrhythmia threshold safety feature, after receiving the command to deliver ATP therapy, LCP 402 may determine a heart rate based on cardiac signals it receives from the heart. After determining the heart rate, LCP 402 may compare its determined heart rate to the arrhythmia threshold. If the determined heart rate is greater than or equal to the arrhythmia threshold, LCP 402 may proceed to deliver ATP therapy to the heart of the patient. If the determined heart rate is not greater than or equal to the arrhythmia threshold, LCP 402 may not proceed to deliver ATP therapy to the heart of the patient. This arrhythmia threshold safety feature may help prevent unnecessary delivery of ATP therapy to the patient due to heart rate detection errors by the ICD.

Of course, in some example systems, the triggered ATP therapy mode and the arrhythmia threshold safety feature may both be implemented to provide a multi-tiered safety approach. For example, after receiving a command for LCP 402 to deliver ATP therapy, LCP 402 may check if the triggered ATP therapy mode is enabled. Only if LCP 402 determines that the triggered ATP therapy mode is enabled does the LCP 402 determine a heart rate and compare the determined heart rate to the arrhythmia threshold. If LCP 402 determines that the heart rate is equal to or greater than the arrhythmia threshold, the LCP 402 may then be allowed to deliver ATP therapy.

In still other embodiments, again in addition to either the triggered ATP therapy mode or the arrhythmia threshold safety feature, or both, or as an alternative to either, some systems may include an ATP therapy burst count threshold safety feature. In these embodiments, LCP 402 may track the number of ATP therapy bursts that have been delivered as part of ATP therapy delivery. After receiving a command to deliver ATP therapy, and before delivering the ATP therapy, LCP 402 may compare the number of ATP therapy bursts to the ATP therapy burst count threshold. If the number of ATP therapy bursts is less than the ATP therapy burst count threshold, LCP 402 may proceed with delivering the ATP therapy. However, if the number of ATP therapy bursts equals or exceeds the ATP therapy burst count threshold, LCP 402 may not proceed with delivering the ATP therapy.

In some embodiments, an ATP therapy burst may refer to a sequence of delivered pacing pulses, and LCP 402 may deliver multiple ATP therapy bursts during a single delivery of ATP therapy. That is, LCP 402 may use multiple ATP therapy bursts in an attempt to terminate an arrhythmia after being commanded to deliver ATP therapy. However, in other embodiments, a single ATP therapy burst may refer to a single delivery of ATP therapy by LCP 402, even where a single delivery of ATP therapy includes delivering multiple sequences or bursts of pacing pulses.

In some embodiments that include an ATP therapy burst count threshold, the ATP therapy burst counter may be related to a particular time frame. For instance, the ATP therapy burst count threshold may be a threshold for a delivery of a number of ATP therapy bursts within a time frame such as one hour, two hours, twelve hours, twenty-four hours, or any other suitable time frame. Upon delivering a first ATP therapy burst, LCP 402 may begin a timer and increment the ATP therapy burst counter. Upon delivery of each subsequent ATP therapy burst, LCP 402 may increment the ATP therapy burst counter and compare the value of the ATP therapy burst counter with the ATP therapy burst count threshold. If the value of the ATP therapy burst counter equals or exceeds the ATP therapy burst count threshold, LCP 402 may not deliver the ATP therapy. Upon the timer reaching the end of the predetermined time frame, LCP 402 may reset both the ATP therapy burst counter and the timer back to zero. The timer may begin running again upon being reset or upon the next delivery of an ATP therapy burst. As one illustrative embodiment, the ATP therapy burst count threshold may have a value of ten ATP therapy bursts, and the timer may have a reset period of twenty-four hours. In this embodiment, if LCP 402 determines that the timer is on hour twenty, and that the ATP therapy burst counter is at ten, LCP 402 may determine the number of ATP therapy bursts equals or exceeds the ATP therapy burst count threshold. In such an embodiment, LCP 402 may not deliver ATP therapy. After the timer reaches twenty-four hours, LCP 402 may reset the timer and the ATP therapy burst counter.

It should be understood that the use of ten ATP therapy bursts as a value for the ATP therapy burst count threshold and a time frame of twenty four hours is just one embodiment. The ATP therapy burst count threshold may have any suitable value for any time frame. Additionally, in other embodiments, instead of keeping a running timer based on when ATP therapy was delivered, LCP 402 may track the number of ATP therapy bursts based on a time of day. For instance, if the time frame is hourly, LCP 402 may reset the ATP therapy burst counter at the beginning of each hour (or after each elapsed time of one hour).

In embodiments where LCP 402 is capable of two-way communication, after determining that the ATP therapy burst counter exceeds the ATP therapy burst count threshold for the allotted time frame, LCP 402 may communicate an error message. The error message may be communicated to a user of the system (either by being directly received by a device external to the patient or relayed through the ICD), and the user may take appropriate action.

In at least some embodiments, the ICD may track the number of commands sent to LCP 402 to delivery ATP therapy and the number of ATP therapies delivered by LCP 402. The ICD may additionally compare the tracked number of communicated commands to the number of delivered ATP therapies. If the ICD determines a difference between the two values equal to or greater than a threshold, the ICD may communicate an error message to another device and/or take other actions.

Of course, the ATP therapy burst count threshold safety feature may be combined with either the triggered ATP therapy mode safety feature or the arrhythmia threshold safety feature, or both, to provide a multi-layered safety feature. For example, when paired with the triggered ATP therapy mode, after receiving a command for LCP 402 to deliver ATP therapy, LCP 402 may first check if the triggered ATP therapy mode is enabled. Only if LCP 402 determines that the triggered ATP therapy mode is enabled does the LCP 402 increase the ATP therapy burst counter and compare the ATP therapy burst counter to the ATP therapy burst count threshold. If LCP 402 determines that the ATP therapy burst counter is less than the ATP therapy burst count threshold, the LCP 402 is allowed to proceed with delivering ATP therapy. Alternatively, the ATP therapy burst count threshold safety feature may be paired with the arrhythmia threshold safety feature. In such embodiments, after receiving a command to deliver ATP therapy, LCP 402 may determine a heart rate and compare the determined heart rate to the arrhythmia threshold. If LCP 402 determines that the heart rate is equal to or greater than the arrhythmia threshold, LCP 402 may be allowed to proceed to increase the ATP therapy burst counter. After increasing the ATP therapy burst counter, LCP 402 may compare the ATP therapy burst counter to the ATP therapy burst count threshold. If LCP 402 determines that the ATP therapy burst counter is less than the ATP therapy burst count threshold, LCP 402 may be allowed to proceed with delivering ATP therapy.

Figure 7:
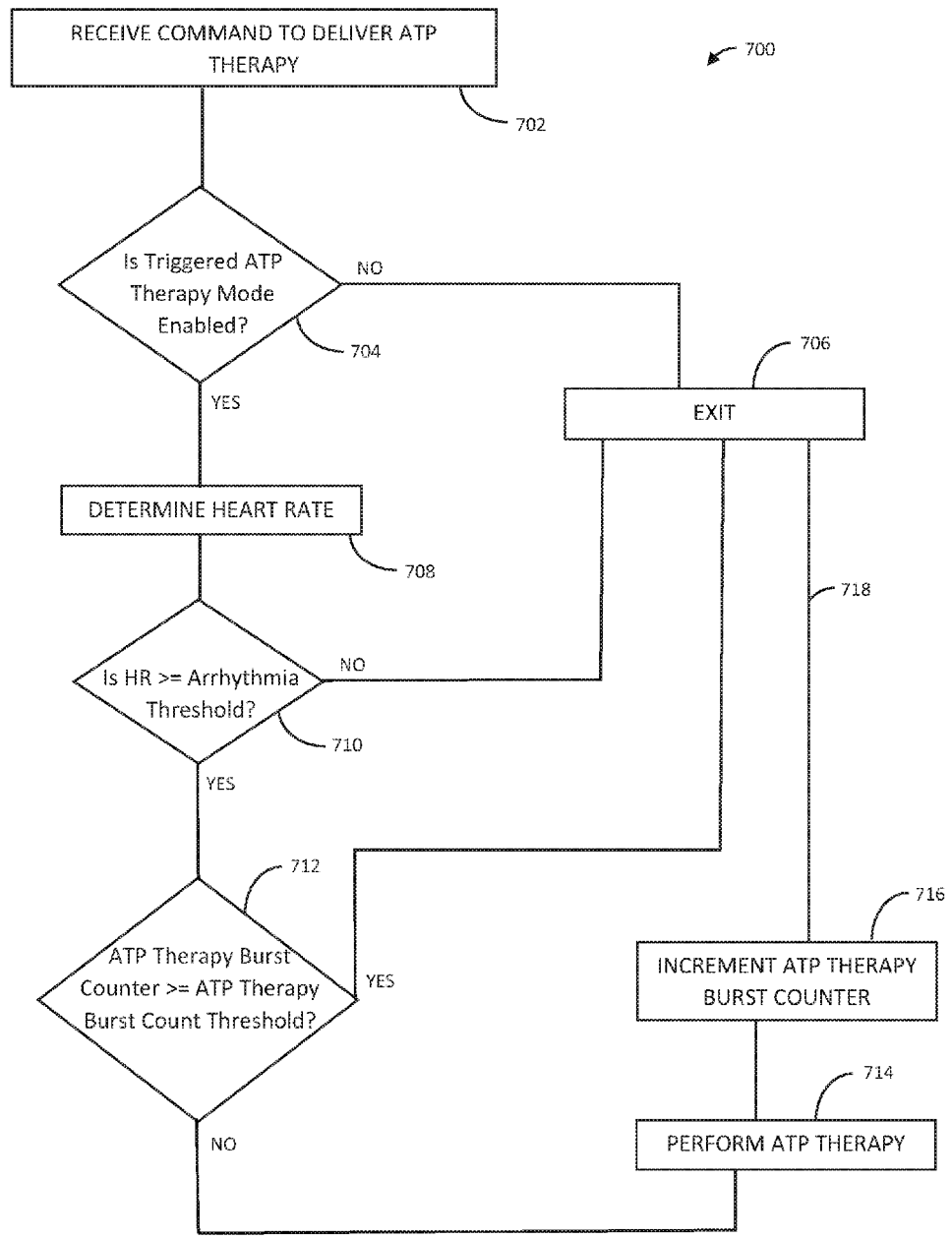
FIG. 7 is a flow diagram of an illustrative method that may be implemented by a medical device or medical device system, such as the illustrative medical devices and medical device systems described with respect to FIGS. 1-5.

In still other embodiments, all three of the triggered ATP therapy mode safety feature, the arrhythmia threshold safety feature, and the ATP therapy burst count threshold safety feature may be combined in a multi-tiered manner. One embodiment of how the safety features may be combined is illustrated in the flow diagram of FIG. 7. The flow diagram in FIG. 7 illustrates an example method 700 that may be implemented by LCP 402 before delivering ATP therapy. Flow diagram 700 begins at step 702, where LCP 402 receives a command to delivery ATP therapy. At block 704, the LCP 402 may determine whether its triggered ATP therapy mode is enabled.

If LCP 402 determines that the triggered ATP therapy mode is not enabled, LCP 402 may exit out of the flow diagram without performing ATP therapy, as shown at 706. If, however, LCP 402 determines that triggered ATP therapy mode is enabled, LCP 402 may proceed to determine a heart rate, as shown at 708. After determining a heart rate, LCP 402 may determine whether the heart rate is equal to or greater than an arrhythmia threshold, as shown at 710. If LCP 402 determines that the heart rate is less than the arrhythmia threshold, LCP 402 may exit out of the flow diagram without performing ATP therapy, as shown at 706.

If LCP 402 determines that the heart rate is equal to or greater than the arrhythmia threshold, LCP 402 may proceed to determine if an ATP therapy burst counter is equal to or greater than the ATP therapy burst count threshold, as shown at 712. If LCP 402 determines that the ATP therapy burst counter is equal to or greater than the ATP therapy burst count threshold, LCP 402 may exit out of the flow diagram without performing ATP therapy, as shown at 706. However, if LCP 402 determines that the ATP therapy burst counter is less than the ATP therapy burst count threshold, LCP 402 may proceed to deliver an ATP therapy burst, as shown at 714. LCP 402 may additionally increment ATP therapy burst counter, as shown at 716. Although block 716 is depicted after block 714, in other embodiments, block 716 may occur before block 714, or in a substantially simultaneous manner. After delivering ATP therapy, LCP 402 may exit out of the flow diagram, as shown at 706.

Of course, in other embodiments, the specific blocks detailed in FIG. 7 may be performed in different orders. For example, LCP 402 may determine whether the ATP therapy burst counter equals or exceeds the ATP therapy burst count threshold before determining a heart rate and whether the heart rate is equal to or greater than the arrhythmia threshold. In some embodiments, LCP 402 may also increase a therapy request counter in addition to the ATP therapy burst counter. In embodiments where the ICD also tracks the number of commands to deliver ATP therapy it sends to LCP 402, this therapy request counter may be useful for determining whether LCP 402 is receiving erroneous commands to perform ATP therapy.

In some embodiments, after delivering ATP therapy, LCP 402 may wait for a shock and enter a post shock pacing mode. In the post shock pacing mode, LCP 402 may deliver pacing pulses to the heart of the patient. Generally, LCP 402 may deliver the pacing pulses at a rate slower than during the delivered ATP therapy bursts. However, LCP 402 may deliver the pacing pulses at a higher rate than when in a normal pacing mode, but this is not required. Additionally, in some embodiments, the pulse amplitude of the delivered pacing pulses while LCP 402 is in the post shock pacing mode may be greater than the pulse amplitude of the pacing pulses delivered by LCP 402 when not in the post shock pacing mode—e.g. when LCP 402 is in a normal pacing mode. In even other embodiments, the pulse width of the delivered pacing pulses while LCP 402 is in the post shock pacing mode may be greater than the pulse width of the pacing pulses delivered by LCP 402 when not in the post shock pacing mode. Of course, in still other embodiments, both of the pulse amplitude and the pulse width of the delivered pacing pulses may be elevated relative to a normal pacing mode. In various embodiments, LCP 402 may remain in the post shock pacing mode between about thirty to sixty seconds, or any other suitable period of time, after delivering ATP therapy. After exiting the post shock pacing mode, LCP 402 may revert to a normal pacing mode.

Figure 8:
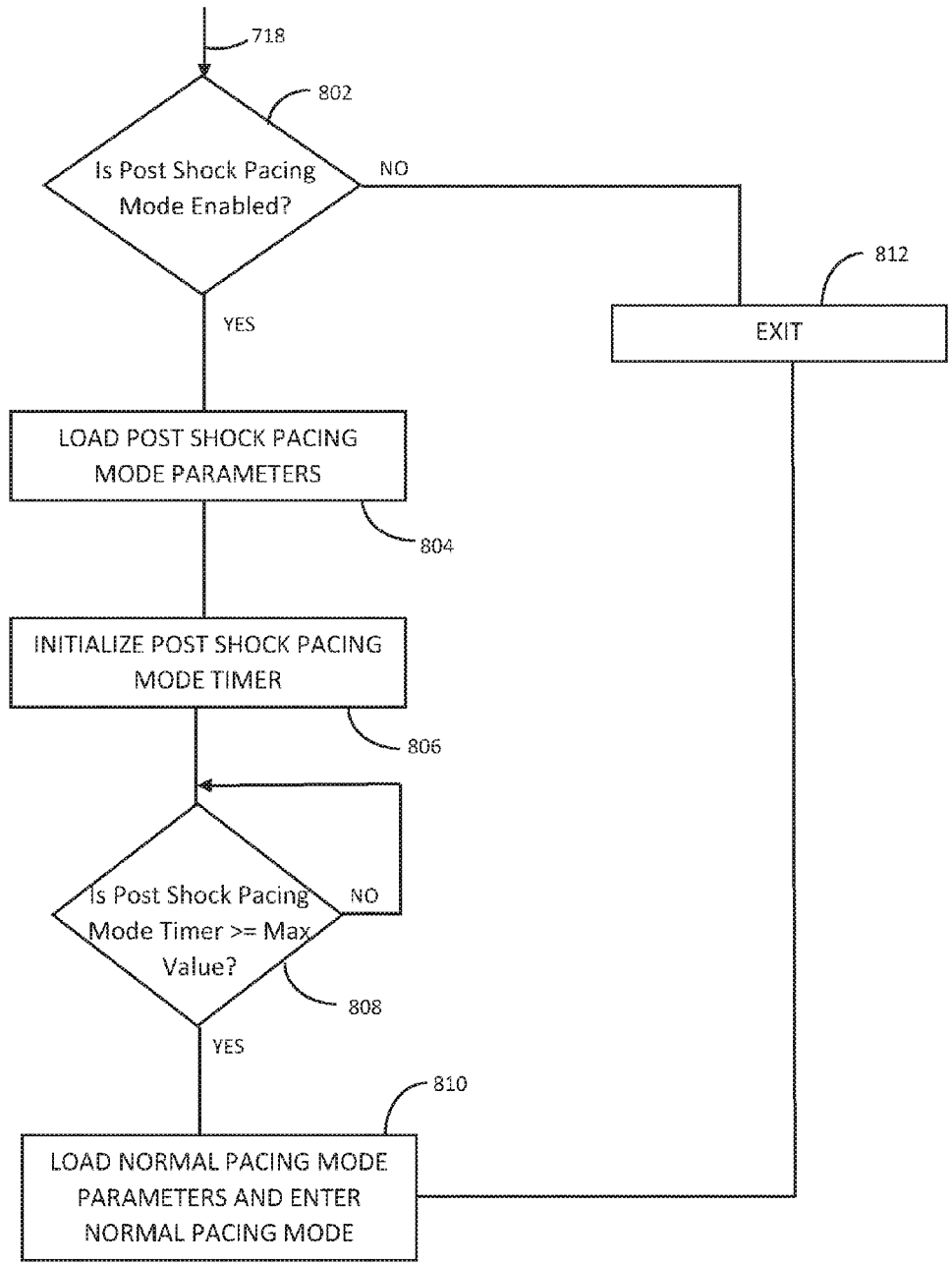
FIG. 8 is a flow diagram of another illustrative method that may be implemented by a medical device or medical device system, such as the illustrative medical devices and medical device systems described with respect to FIGS. 1-5

FIG. 8 is a flow diagram of an illustrative post shock pacing mode 800 of an illustrative LCP 402. In some embodiments, post shock pacing mode 800 may be a branch of flow chart 700. For example, after LCP 402 delivers ATP therapy, instead of exiting the flow diagram at 706, branch 718 of FIG. 7 may flow into step 802 of post shock pacing mode 800. When so provided, after delivering ATP therapy, LCP 402 may determine whether a post shock pacing mode of the LCP 402 is enabled, as shown at 802. In some embodiments, the received command to deliver ATP therapy may also include an instruction to enable or disable a post shock pacing mode. In such embodiments, the ICD may only need to send a single communication to LCP 402 to both command LCP 402 to deliver ATP therapy and to indicate that LCP 402 should enter, or not enter, a post shock pacing mode after delivering the ATP therapy. In other embodiments, whether the post shock pacing mode is enabled may be a programmable parameter, as will be discussed subsequently. If LCP 402 determines that the post shock pacing mode is disabled, then LCP 402 may exit the flow diagram, as shown at 812.

However, if LCP 402 determines that the post shock pacing mode is enabled, LCP 402 may load post shock pacing mode parameters, as shown at 804. In some embodiments, the post shock pacing mode parameters include a pacing pulse amplitude. In other embodiments, the post shock pacing mode parameters include a pacing pulse width. In still other embodiments, the post shock pacing mode parameters include a pacing rate of the pacing pulses to be delivered while in the post shock pacing mode. Of course, in yet other embodiments, the post shock pacing mode parameters may include any combination of these parameters. The post shock pacing mode parameters may be preprogrammed into a memory of LCP 402. Although, in other embodiments, the command from the ICD to LCP 402 to deliver ATP therapy may include one or more post shock pacing mode parameters.

After loading the post shock pacing mode parameters, LCP 402 may initialize a post shock pacing mode timer, as at 806. LCP 402 may then enter loop 808 to determine when the post shock pacing mode timer has reached the post shock pacing mode timer max value, which corresponds to the length of time LCP 402 is in the post shock pacing mode. After determining that the post shock pacing mode timer has reached its maximum value, LCP 402 loads the normal pacing mode parameters and returns to the normal pacing mode, as shown at 810, and exits the flow diagram at 812.

In some additional, or alternative embodiments, the system of LCP 402 and the ICD may include the ability to distinguish between different types of arrhythmias. For instance, the ICD may have one or more normal beat templates stored in memory. After determining a potential occurrence of an arrhythmia, for example by comparing a determined heart rate to a heart rate threshold, the ICD may isolate a QRS complex of the current beat from sensed cardiac electrical signals. The ICD may then compare the QRS of the current beat to the normal beat template. For example, the ICD may perform a correlation analysis between the current beat and the normal beat template. If the correlation between the beats is equal to or greater than a first correlation threshold, the ICD may determine that no arrhythmia is occurring.

However, if the correlation between the beats is less than a first correlation threshold, the ICD may further isolate the QRS complex from a previous beat (or capture a new current beat and use the beat it compared with the normal beat template as the previous beat). The ICD may then compare the current beat with the previous beat. For example, the ICD may perform a correlation analysis between the two beats. If the ICD determines that the correlation between the two beats is equal to or greater than a second correlation threshold, the ICD may determine that the arrhythmia is a Monomorphic Ventricular Tachycardia (MVT). If the ICD determines that the correlation between the two beats is less than a second correlation threshold, the ICD may further compare the width of the QRS complex of the current beat with the width of the QRS complex of the normal beat template. If the width of the QRS complex of the current beat is narrower than the QRS complex of the normal beat template, the ICD may determine that the arrhythmia is a Supraventricular Tachycardia (SVT). If the width of the QRS complex of the current beat is wider than the QRS complex of the normal beat template, the ICD may determine that the arrhythmia is a Polymorphic Ventricular Tachycardia (PVT).

Where the ICD is able to determine a type of the tachycardia, the ICD may communicate with LCP 402 to deliver different electrical stimulation therapy. For instance, in some embodiments, if the ICD determines that the type of arrhythmia is a PVT or an SVT, the ICD may not communicate a command to LCP 402 to deliver ATP therapy. Instead, the ICD may deliver defibrillation and/or cardioversion therapy to the heart to treat the arrhythmias. If the ICD determines that the type of arrhythmia is an MVT, then the ICD may communicate a command to LCP 402 to deliver ATP therapy. However, in other embodiments, the ICD may communicate a command to LCP 402 if the ICD determines that the arrhythmia is an SVT and/or a PVT.

In still other embodiments, the ICD may coordinate delivery of electrical stimulation therapy with LCP 402 based on the determined type of arrhythmia. For instance, if the determined type of arrhythmia is an MVT, the ICD may communicate a command to LCP 402 to deliver ATP therapy but may not begin charging its charge storage device for delivery of defibrillation and/or cardioversion therapy. Instead, the ICD may monitor received cardiac electrical signals during and after the ATP therapy delivered by LCP 402. The ICD may determine, based on the received cardiac electrical signals, whether the delivered ATP therapy has terminated the arrhythmia. If the ICD determines that the ATP therapy did not terminate the arrhythmia, the ICD may then begin to charge is charge storage device and deliver defibrillation and/or cardioversion therapy once the charge storage device is charged.

Where the ICD determines that the type of arrhythmia is a PVT or an SVT, the ICD may still send the command to LCP 402 to deliver ATP therapy. However, along with sending the command, the ICD may also being charging its charge storage device for delivery of defibrillation and/or cardioversion therapy. The ICD may also monitor received cardiac electrical signals while charging its charge storage device and during and after LCP 402 delivers ATP therapy. If the ICD determines that the ATP therapy successfully terminated the arrhythmia, the ICD may cease charging its charge storage device and may not deliver defibrillation and/or cardioversion therapy. However, if the ICD determines that the ATP therapy did not terminate the arrhythmia, the ICD may complete charging its charge storage device and deliver defibrillation and/or cardioversion therapy. In these embodiments, the ICD may preserve battery life by only initiating charging upon detection of an arrhythmia for certain types of arrhythmias. Of course, in other embodiments, the ICD may wait to initiate charging if the determined type of arrhythmia is also an MVT and/or SVT. In still other embodiments, the ICD may initiate charging when the determined type of arrhythmia is an MVT.

In additional, or alternative, embodiments where the ICD may discriminate between various arrhythmia types, the ICD may further communicate different ATP therapy parameters to LCP 402. As discussed above, the ICD may include ATP therapy parameters in the command to deliver ATP therapy. Accordingly, if the ICD determines that the type of arrhythmia is an MVT, the ICD may communicate ATP therapy parameters different than those that the ICD would communicate if the determine type of arrhythmia is a PVT and/or an SVT.

In some embodiments, LCP 402 may have stored in memory different ATP therapy parameters associated with the different arrhythmia types. In such embodiments, instead of the ICD communicating specific ATP therapy parameters, the ICD may merely communicated a determined type of arrhythmia. In still other embodiments, LCP 402 may be able to discriminate between different arrhythmia types. In such embodiments, instead of the ICD communicating ATP therapy parameters or a type of arrhythmia, LCP 402 may determine a type of arrhythmia and used the ATP therapy parameters stored in its memory that are associated with that type of arrhythmia.

As discussed with respect to FIGS. 4 and 5, the systems that may implement these disclosed techniques may, at some times, be in communication with an external support device, such as external support devices 420 and 520. When an external support device is in communication with a medical device system implementing one or more of the disclosed techniques, such as the system of FIG. 4, a user may interact with the external support device to program various features of the devices. For example, a user may interact with the external support device to enable or disable the triggered ATP therapy mode of LCP 402. The user may set or adjust the values of arrhythmia threshold, the ATP therapy burst count threshold, the time frame associated with the ATP therapy burst count threshold, the various ATP therapy parameters, the associations between the ATP therapy parameters and the arrhythmia types, the length of the post shock pacing mode timer, and the other various parameters discussed herein.

Additionally, although many of the above described techniques were described with respect to a system including and LCP and an ICD (again, which could be either a non-subcutaneously implanted device or a subcutaneously implanted device—e.g. an SICD), the disclosed techniques may be implemented in a variety of other systems. For instance, many of the disclosed techniques were described as being implemented by LCP 402. In other systems, other devices that provide electrical stimulation therapy and receive commands to deliver the electrical stimulation therapy may implement one or more of the disclosed techniques—for instance an ICD or SICD or cardiac pacemaker that receives commands from another device to delivery electrical stimulation therapy. In systems that include more than two devices, two or more of the devices of the system may individually implement one or more of the disclosed techniques. For instance, some system may include multiple LCPs. In such systems, each LCP may individually perform one or more of the disclosed techniques before delivering ATP therapy.

Further, the disclosed techniques should also not be viewed as limited to only ATP therapy. In other embodiments, medical device system may operate to provide other types of electrical stimulation therapy. Such systems may also implement one or more of the disclosed techniques except, instead of performing one or more of the disclosed techniques before delivering ATP therapy, the devices may perform one or more of the disclosed techniques before delivering other electrical stimulation therapy, such as CRT, defibrillation and/or cardioversion therapy, bradycardia therapy, and other types of electrical stimulation therapy.

In general, those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules. Accordingly, departure in form and detail may be made without departing from the scope and spirit of the present disclosure as described in the appended claims.

What is claimed is:

1. A leadless cardiac pacemaker (LCP) comprising:
a housing;
a plurality of electrodes for sensing electrical signals emanating from outside of the housing;
an energy storage module disposed within the housing;
a control module disposed within the housing and operatively coupled to the plurality of electrodes, wherein the control module is configured to:
receive electrical signals via two or more of the plurality of electrodes;
determine whether the received electrical signals are indicative of a command for the LCP to deliver anti-tachyarrhythmia pacing (ATP) therapy;
when the received electrical signals are indicative of a command for the LCP to deliver anti-tachyarrhythmia pacing (ATP) therapy, determine whether a triggered ATP therapy mode of the LCP is enabled;
when the received electrical signals are indicative of a command for the LCP to deliver ATP therapy and the triggered ATP therapy mode is enabled, deliver ATP therapy via two or more of the plurality of electrodes; and
when the received electrical signals are indicative of a command for the LCP to deliver therapy and the LCP is in a safe mode in which the triggered ATP therapy mode is not enabled, not delivering ATP therapy via two or more of the plurality of electrodes.

2. The LCP of claim 1, wherein when the triggered ATP therapy mode is enabled, the control module of the LCP is further configured to determine whether to deliver ATP therapy before delivering the ATP therapy via the two or more of the plurality of electrodes, and wherein the control module is configured to determine to deliver ATP therapy based at least in part on whether a heart rate, determined from the received electrical signals, is above an arrhythmia threshold, and when the control module determines to deliver the ATP therapy, the control module delivers the ATP therapy via the two or more of the plurality of electrodes.

3. The LCP of claim 1, wherein the control module is configured to maintain a count of a number of ATP therapy bursts that have been delivered as part of the delivered ATP therapy, and wherein the control module is further configured to continue to deliver ATP therapy when the number of ATP therapy bursts has not exceeded a ATP therapy burst count threshold.

4. The LCP of claim 1, wherein the control module is configured to determine a signal morphology type of a cardiac signal received via two or more of the plurality of electrodes, and wherein when the triggered ATP therapy mode is enabled, the control module of the LCP is further configured to determine whether to deliver ATP therapy before delivering the ATP therapy via the two or more of the plurality of electrodes, and wherein the control module is configured to determine to deliver ATP therapy based at least in part on whether the determined signal morphology type is of a predetermined signal morphology type, and when the control module determines to deliver the ATP therapy, the control module delivers the ATP therapy via the two or more of the plurality of electrodes.

5. The LCP of claim 4, wherein the predetermined signal morphology type comprises a Monomorphic Ventricular Tachycardia (MVT).

6. The LCP of claim 4, wherein the predetermined signal morphology type comprises a Polymorphic Ventricular Tachycardia (PVT).

7. The LCP of claim 4, wherein the predetermined signal morphology type comprises a Supra Ventricular Tachycardia (SVT).

8. A leadless cardiac pacemaker (LCP) comprising:
a housing;
a plurality of electrodes for sensing electrical signals emanating from outside of the housing;
an energy storage module disposed within the housing;
a control module disposed within the housing and operatively coupled to the plurality of electrodes, wherein the control module is configured to:
receive electrical signals via two or more of the plurality of electrodes;
determine whether the received electrical signals are indicative of a command for the LCP to deliver anti-tachyarrhythmia pacing (ATP) therapy;
when the received electrical signals are indicative of a command for the LCP to deliver anti-tachyarrhythmia pacing (ATP) therapy, deliver ATP therapy via two or more of the plurality of electrodes;
maintain a measure related to an amount of ATP therapy delivered as part of the delivered ATP therapy within a predetermined period of time;
continue to allow delivery of ATP therapy when the measure related to the amount of ATP therapy delivered within the predetermined period of time has not exceeded a predetermined ATP therapy threshold; and
stop delivery of ATP therapy when the measure related to the amount of ATP therapy delivered within the predetermined period of time has exceeded the predetermined ATP therapy threshold.

9. The LCP of claim 8, wherein the predetermined period of time is between one hour and twenty-four hours.

10. The LCP of claim 8, wherein the measure related to the amount of ATP therapy delivered as part of the delivered ATP therapy within the predetermined period of time corresponds to an ATP therapy delivered count that is indicative of a number of times a command is received that results in the LCP delivering ATP therapy within the predetermined period of time.

11. The LCP of claim 8, wherein the measure related to the amount of ATP therapy delivered as part of the delivered ATP therapy within the predetermined period of time corresponds to an ATP burst count that is indicative of a number of ATP bursts that are delivered within the predetermined period of time.

12. The LCP of claim 8, wherein the received electrical signals comprise a plurality of communication pulses produced by a remote medical device.

13. The LCP of claim 8, wherein the received electrical signals comprise a plurality of communication pulses as part of a one-way communication path from a remote medical device.

14. The LCP of claim 13, wherein the plurality of communication pulses are free from error checking information for error checking the one-way communication path.

15. The LCP of claim 8, wherein after delivering ATP therapy, the LCP is further configured to enter a post shock pacing mode.

16. A leadless cardiac pacemaker (LCP) comprising:
a housing;
a plurality of electrodes for sensing electrical signals emanating from outside of the housing;
an energy storage module disposed within the housing;
a control module disposed within the housing and operatively coupled to the plurality of electrodes, wherein the control module is configured to:
receive electrical signals via two or more of the plurality of electrodes;
determine whether the received electrical signals are indicative of a command for the LCP to deliver anti-tachyarrhythmia pacing (ATP) therapy;
when the received electrical signals are indicative of a command for the LCP to deliver anti-tachyarrhythmia pacing (ATP) therapy:
determine whether a triggered ATP therapy mode of the LCP is enabled;
determine whether a heart rate determined from the received electrical signals is above an arrhythmia threshold;
when the triggered ATP therapy mode is enabled and the heart rate is above the arrhythmia threshold, deliver ATP therapy via two or more of the plurality of electrodes; and
when either the triggered ATP therapy mode is not enabled or the heart rate is not above the arrhythmia threshold, not delivering ATP therapy via two or more of the plurality of electrodes.

17. The LCP of claim 16, wherein the control module maintains a measure related to the amount of ATP therapy delivered within a predetermined period of time, and wherein the control module is configured to determine whether the measure related to the amount of ATP therapy delivered within the predetermined period of time exceeds a predetermined ATP therapy threshold, and only delivers ATP therapy via two or more of the plurality of electrodes when the triggered ATP therapy mode is enabled, the heart rate is above the arrhythmia threshold, and the measure related to the amount of ATP therapy delivered within the predetermined period of time does not exceed the predetermined ATP therapy threshold.

18. The LCP of claim 17, wherein the predetermined period of time is between one hour and twenty-four hours.

* * * * *